United States Patent [19]

Guglielmetti et al.

[11] Patent Number: 5,529,725
[45] Date of Patent: Jun. 25, 1996

[54] SPIROOXAZINES AND USE THEREOF IN THE FIELD OF OPHTHALMIC OPTICS

[75] Inventors: Robert Guglielmetti; André Samat; Pierre Lareginie, all of Marseilles, France

[73] Assignee: Essilor International, Charenton Cedex, France

[21] Appl. No.: 343,958

[22] Filed: Nov. 17, 1994

[30] Foreign Application Priority Data

Nov. 17, 1993 [FR] France ................... 93 13731

[51] Int. Cl.⁶ .................. G02B 5/23; C07D 265/00
[52] U.S. Cl. ................................. 252/586; 544/71
[58] Field of Search .................. 252/586–589; 544/71

[56] References Cited

U.S. PATENT DOCUMENTS 5,349,065  9/1994  Tanaka et al. ................... 252/586

FOREIGN PATENT DOCUMENTS 0407237  7/1994  France .
0388660  7/1994  France .
3234788  10/1991  Japan .

*Primary Examiner*—Philip Tucker
*Attorney, Agent, or Firm*—Keck, Mahin & Cate

[57] ABSTRACT

The invention relates to photochromic compounds of general formula:

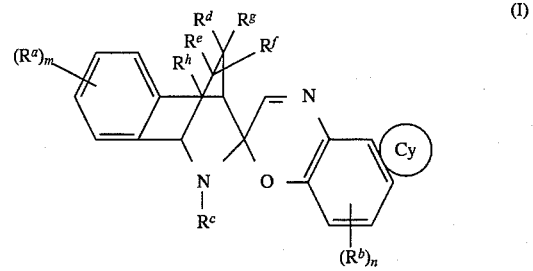

in which:

$R^a$ and $R^b$ denote hydrogen; alkyl; OR, SR, COR or COOR where R denotes hydrogen, alkyl, aryl or heteroaryl; a group $NR_1R_2$ where $R_1 R_2$ denotes hydrogen, $C_4-C_7$ alkyl or cycloalkyl, aryl, or form with the nitrogen a $C_4-C_7$ heterocycle; $NO_2$, CN, SCN or a halogen; a group $SO_3R'$ where R' denotes hydrogen or an alkali metal; a mono- or polyhaloalkyl; m denotes an integer from 1 to 4 and n is equal to 1 or 2;

Cy denotes an aromatic ring or an aromatic or non-aromatic heterocycle;

$R^c$ denotes an alkyl, allyl, phenyl or arylalkyl group which is mono- or disubstituted with alkyl, alkoxy or $NO_2$; an alicyclic, an aliphatic hydrocarbon containing one or more hetero atoms;

$R^d$, $R^e$, $R^f$ and $R^g$ denote hydrogen, alkyl, alkoxy or thioalkyl or form in pairs a 4- to 7-membered cycloalkyl possibly containing hetero atoms which are optionally condensed with an aromatic ring; $R^h$ denotes hydrogen or forms with $R^d$ a 5- or 6-membered cycloalkyl; and the use thereof in ophthalmic optics.

12 Claims, No Drawings

SPIROOXAZINES AND USE THEREOF IN THE FIELD OF OPHTHALMIC OPTICS

FIELD OF THE INVENTION

The invention relates to novel photochromic compounds, more particularly photochromic compounds containing a ring from the spirooxazine family in their chemical formula, and the use thereof in the field of ophthalmic optics, in particular in and/or on ophthalmic lenses.

BACKGROUND OF THE INVENTION

The phenomenon of photochromism has been known for many years. A compound is said to be photochromic when, after irradiation with a light beam certain wavelengths of which are situated in the ultraviolet range, this compound changes colour and returns to its original colour once the irradiation is stopped.

This phenomenon has many applications, but one of the more particularly advantageous known applications relates to the field of ophthalmic optics.

Such compounds may be used in the production of lenses or glass for spectacles in order to filter light radiations depending on their intensity.

By incorporating photochromic compounds into an organic material constituting an ophthalmic lens, it is possible to obtain a glass of considerably reduced weight relative to conventional lenses made of inorganic glass which contain silver halides as photochromic agent. Their incorporation into organic materials has always posed technical difficulties.

However, not all compounds with photochromic properties are necessarily usable in the field of ophthalmic optics. Indeed, the photochromic compound must fulfil a certain number of criteria, some of which are:

- strong colorability, which is a measurement of the capacity of a photochromic compound to show an intense colour after isomerization;
- a coloration after absorption of light, which renders the photochromic compound capable of being used, alone or in combination with other photochromic compounds, in ophthalmic glass or lenses;
- an absence of coloration, or very little coloration, in the initial form;
- rapid coloration or decoloration kinetics;
- a photochromism exhibited in the widest possible temperature range, and in particular preferably between 0° and 40° C.

The organic photochromic compounds currently known and used generally show decreasing photochromism as the temperature rises, such that the photochromism is particularly pronounced at temperatures close to 0° C., whereas it is much weaker, or even non-existent, at temperatures of the order of 40° C., which are temperatures which the glass may reach especially on exposure to the sun.

Another problem encountered by the photochromic compounds of the state of the art is their lifetime. Indeed, for certain products of the state of the art, a relatively short lifetime is observed. In effect, after a certain number of coloration and decoloration cycles, the photochromic compound becomes blocked generally in an open and coloured form and no longer displays reversible photochromic properties.

The photochromic properties of spirooxazines have been described by R. E. Fox in the document Final Report of Contact AF 41, A.D. 440226 1961, 657.

Compounds of spiro(indoline-naphthooxazine) type have been synthesized and described in particular in the article by N. Y. C. Chu "Photochromism: Molecules and Systems" Ed. H. Dürr, H. Bovas Laurent, Elsevier, Amsterdam 1990, ch. 24, and compounds of spiro(indoline-quinazolinooxazine) or spiro(indoline-benzothiazolooxazine) type in U.S. Pat. Nos. 5,139,707 and 5,114,621 (R. Guglielmetti, P. Tardieu) filed in the name of the company ESSILOR.

SUMMARY OF THE INVENTION

A novel family of spirooxazines is described which show particularly advantageous photochromic properties. Indeed, among the compounds belonging to this family, a great many compounds show strong colorability, especially in the red field which is particularly useful for ophthalmic optics, these compounds possibly being used with photochromic compounds giving a blue colour with a view to obtaining a natural final coloration on exposure to light. Moreover, in their coloured form, they show a larger hypsochromic shift as regards absorption of light, and a colorability which is similar to or reinforced with respect to the spirooxazine compounds known in the state of the art.

Other spirooxazine compounds according to the invention have, in their coloured form, a colour resulting from a very broad absorption band in the visible region. The use of these specific compounds in ophthalmic optics makes it possible to limit the number of photochromic compounds of different nature to be used in order to obtain specific tints in the usual photochromic glasses.

Furthermore, the compounds in accordance with the invention have no coloration, or very little coloration, in the initial state and show rapid coloration and decoloration kinetics across a very broad temperature range, between 0° and 40° C. in particular.

The Applicant has also observed that these compounds had a particularly long lifetime.

The effect of all these properties is that these novel photochromic compounds are particularly advantageous in their use in ophthalmic optics and in particular for their use in and/or on ophthalmic lenses.

For the purposes of the invention, ophthalmic lenses refers to the glass of spectacles, in particular of sunglasses, and contact lenses.

One subject of the invention thus consists of the novel photochromic compounds.

Another subject of the invention consists of the use thereof in ophthalmic optics.

The invention also relates to compositions intended to be used for coating ophthalmic lenses or their incorporation into these lenses.

Other subjects of the invention will become apparent on reading the description and the examples which follow.

DETAILED DESCRIPTION OF THE PREFERRED EMBODIMENTS

The photochromic compound in accordance with the invention is essentially characterized in that it corresponds to the general formula:

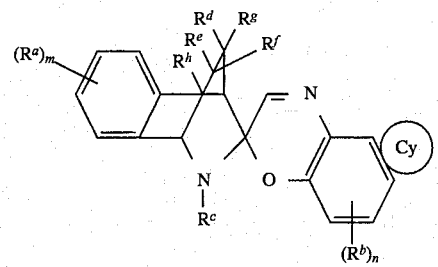

(I)

in which

R$^a$ and R$^b$ denote, independently of each other, a hydrogen atom; an alkyl group; a group OR, SR, COR or COOR or SO$_2$R in which groups R denotes a hydrogen atom or an alkyl, aryl or heteroaryl group; an amino group NR$_1$R$_2$ in which R$_1$ and R$_2$ denote, independently of each other, a hydrogen atom, an alkyl group, a cycloalkyl group or an aryl group, R$_1$ and R$_2$ possibly forming, with the nitrogen atom, a 4- to 7-membered heterocycle and also possibly containing one or more hetero atoms chosen from sulphur, oxygen and nitrogen; a halogen atom, a C$_1$–C$_4$ monohaloalkyl group; a C$_1$–C$_4$ polyhaloalkyl group; a group NO$_2$, CN or SCN; SO$_3$R' where R' denotes hydrogen or an alkali metal;

m denotes an integer from 1 to 4 and n is equal to 1 or 2 depending on the number of substitutions on the ring;

Cy denotes an aromatic ring, preferably a 5- or 6-membered aromatic ring, which may be substituted with one or more groups having the meaning of R$^a$, or an aromatic or non-aromatic 4- to 7-membered heterocycle containing one or more hetero atoms chosen from nitrogen, oxygen and sulphur;

R$^c$ denotes an alkyl group; an allyl, phenyl or arylalkyl group which is mono- or disubstituted with substituents of alkyl, alkoxy or NO$_2$ type; an optionally substituted alicyclic group; an aliphatic hydrocarbon group containing one or more hetero atoms such as oxygen, sulphur or nitrogen in its chain;

R$^d$, R$^e$, R$^f$ and R$^g$ denote, independently of each other, a hydrogen atom, an alkyl group, an alkoxy group or a thioalkyl group; two of these radicals possibly forming a 4- to 7-membered cycloalkyl or cycloalkenyl group which may contain one or more hetero atoms chosen from nitrogen, sulphur and oxygen and may be condensed with a 5- or 6-membered aromatic ring which may be substituted with one or more radicals having the meaning of R$^a$ and R$^b$.

R$^h$ denotes hydrogen or forms with R$^d$ a 5- or 6-membered cycloalkyl.

Preferably, at least one of the radicals R$^d$ and R$^e$ is not a hydrogen atom.

In the abovementioned formula, the alkoxy and alkyl groups preferably contain 1 to 6 carbon atoms, such as methoxy, ethoxy, methyl, ethyl and propyl; the cycloalkyl groups are preferably cyclohexyl or cyclopentyl; the cycloalkenyl groups are preferably cyclohexenyl or cyclopentenyl; the aryl group is preferably phenyl; the arylalkyl group is preferably benzyl; the polyhaloalkyl group is, for example, CF$_3$; the halogen is especially fluorine, bromine or chlorine.

The 5- or 6-membered aromatic rings are especially phenyl and naphthyl.

The 4- to 7-membered heterocyclic rings are especially pyridine, pyrimidine, indoline, imidazoline or thiazoline rings which are optionally substituted with an alkyl group; a phenyl or amino group; a carbonyl group or a halogen. The aliphatic hydrocarbon group preferably contains an acid, ester or alcohol function.

The preferred compounds of the invention are those of formula (I) for which the radicals R$^a$ and R$^b$ denote H or NO$_2$; Cy denotes a 6-membered aromatic ring which is optionally substituted with an alkoxy; R$^c$ is an alkyl group, preferably methyl; R$^d$, R$^e$, R$^f$ and R$^g$ denote an alkoxy group, preferably ethoxy, or two of these groups form a cylcoalkenyl, preferably cyclopentenyl.

The particularly preferred compounds of the invention are those corresponding to one of the following formulae:

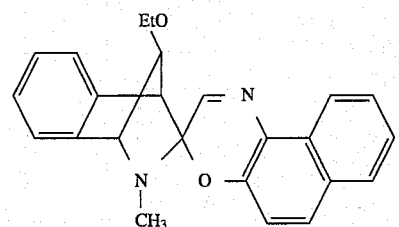

(Ia)

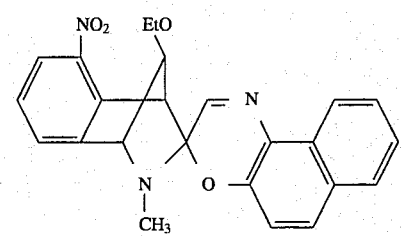

(Ib)

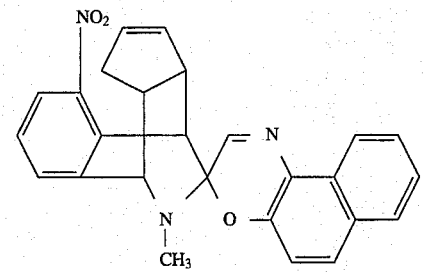

(Ic)

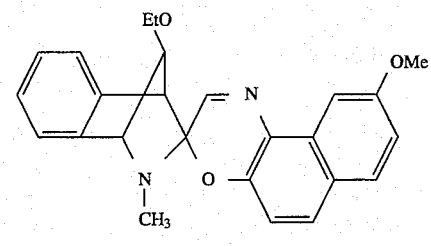

(Id)

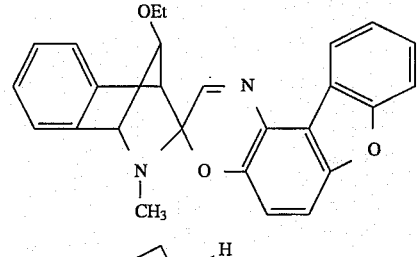

(Ie)

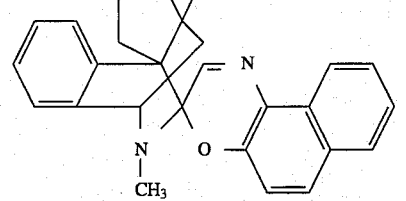

(If)

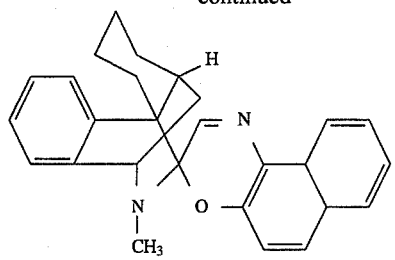

The compounds in accordance with the invention may be prepared according to the following reaction scheme:

REACTION SCHEME A

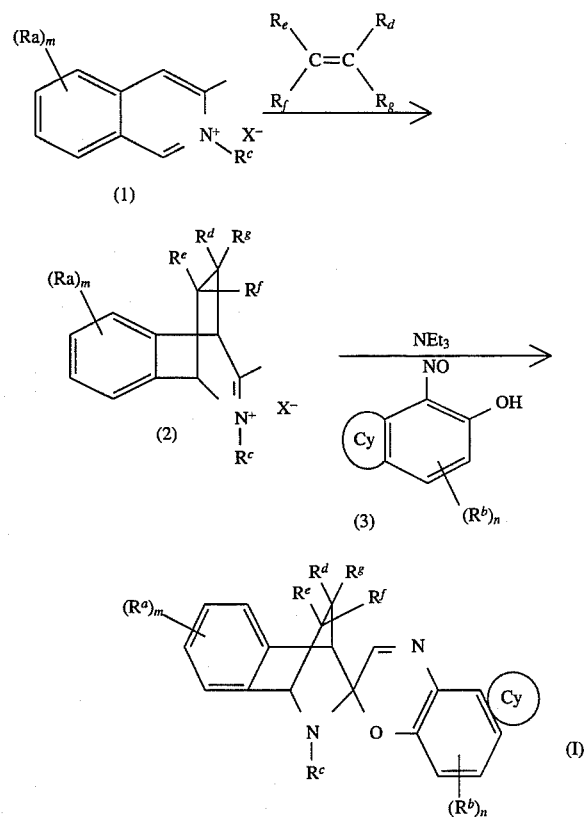

In formulae (1), (2) and (3), the radicals $R^a$, $R^b$, $R^c$, $R^d$, $R^e$, $R^f$, $R^g$ and Cy have the same meanings indicated above and $X^-$ denotes an anion, preferably a halide.

The photochromic compounds of the invention may be used to produce photochromic ophthalmic lenses.

The compounds in accordance with the invention may be introduced into a composition which is intended to be applied to or to be introduced into a transparent organic polymer material in order to obtain a transparent photochromic article. They may also be introduced into solid compositions such as plastic films, sheets and lenses in order to produce materials which may especially be used as ophthalmic lenses, sunglasses, visors, camera optics and filters.

The liquid compositions which constitute one subject of the invention are essentially characterized in that they contain the compounds in accordance with the invention in dissolved or dispersed form in a solvent-based medium, these compounds being suitable for application to or introduction into a transparent polymer material.

Solvents which may more particularly be used are organic solvents chosen from benzene, toluene, chloroform ethyl acetate, methyl ethyl ketone, acetone, ethyl alcohol, methyl alcohol, acetonitrile, tetraydrofuran, dioxane, ethylene glycol methyl ether, dimethylformamide, dimethyl sulphoxide, methylcellosolve, morpholine and ethylene glycol.

When the compounds in accordance with the invention are dispersed, the medium may also contain water.

According to another embodiment, the compounds in accordance with the invention may be introduced into, and preferably dissolved in, colourless or transparent solutions prepared from transparent polymers, transparent copolymers or mixtures of transparent polymers in a suitable organic solvent.

Examples of such solutions are, inter alia, solutions of nitrocellulose in acetonitrile, of polyvinyl acetate in acetone, of polyvinyl chloride in methyl ethyl ketone, of acetylcellulose in dimethylformamide, of polyvinylpyrrolidone in acetonitrile, of polystyrene in benzene, and of ethylcellulose in methylene chloride.

These compositions may be applied to transparent supports, such as supports made of polyethylene glycol terephthalate, of borylated paper, or of cellulose triacetate, and dried in order to obtain a photochromic material, which may become coloured in the presence of ultraviolet radiation and which returns to the colourless and transparent state in the absence of the source of radiation.

The photochromic compounds of the present invention, or the compositions containing them, which are defined above may be applied to or incorporated into a solid transparent polymerized organic material which is suitable for ophthalmic components such as ophthalmic lenses, or into useful materials which may be used in sunglasses, visors, camera optics and filters.

By way of solid transparent materials which may be used to produce ophthalmic lenses in accordance with the invention, there may be mentioned polyol(allyl carbonate) polymers, polyacrylate polymers, poly(alkyl acrylate) polymers such as polymethyl methacrylates, cellulose acetate, cellulose triacetate, cellulose acetate propionate, cellulose acetate butyrate, poly(vinyl acetate), poly(vinyl alcohol), polyurethanes, polycarbonates, polyethylene terephthalates, polystyrenes, poly(styrene - methyl methacrylate)s, copolymers of styrene and acrylonitrile, and polyvinyl butyrates.

The transparent copolymers or mixtures of transparent polymers are also suitable for producing such materials.

There may be mentioned, in this respect, materials prepared from polycarbonates, such as poly(4,4'-dioxyphenyl-2,2-propane carbonate), polymethyl methacrylate, polyol(allyl carbonate)s, in particular such as diethylene glycol bis(allyl carbonate) and the copolymers thereof, for example such as with vinyl acetate. The copolymers of diethylene glycol bis(allyl carbonate) and vinyl acetate (80–90/10–20) may be mentioned in particular, and also the copolymer of diethylene glycol bis(allyl carbonate) with vinyl acetate, cellulose acetate and cellulose propionate, and cellulose butyrate (80–85/15–20).

The polyol(allyl carbonate)s are prepared using the allyl carbonates of linear or branched aliphatic or aromatic liquid polyols, such as the alkylene bis(allyl carbonate) or the aliphatic bis(allyl carbonate) glycols. Among the polyol(allyl carbonate)s that can be used to prepare the solid transparent materials which may be used in accordance with the invention, there may be mentioned ethylene glycol bis(allyl carbonate), diethylene glycol bis(2-methallyl carbonate), diethylene glycol bis(allyl carbonate), ethylene glycol bis (2-chloroallyl carbonate), triethylene glycol bis(allyl carbonate), 1,3-propanediol bis(allyl carbonate), propylene glycol bis(2-ethylallyl carbonate), 1,3-butanediol bis(allyl carbo-nate), 1,4-butanediol bis(2-bromoallyl carbonate), dipropylene glycol bis(allyl carbonate), trimethylene glycol bis(2-ethylallyl carbonate), pentamethylene glycol bis(allyl carbonate), and isopropylenebisphenol bis(allyl carbonate). The most important product consists of diethylene glycol bis(allyl carbonate), also known under the name CR39.

The amount of photochromic compounds to be used in accordance with the invention, either in the composition or at the time of its introduction into the solid support, is not critical and generally depends on the intensity of colour that the composition may impart to the material after exposure to radiation. Generally speaking, the more photochromic compounds are added, the more intense will be the coloration under irradiation.

In accordance with the invention, an amount is used which is sufficient to impart to the treated material the property of changing colour at the time of exposure to radiation. This amount of photochromic compounds is generally between 0.001 and 20% by weight, and preferably between 0.05 and 10% by weight, relative to the total weight of the optical material or of the composition.

The photochromic compounds in accordance with the invention may also be introduced into a temporary transfer support (such as a varnish which forms a coating on a substrate) and then be thermally transferred into the substrate, as described in particular in U.S. Pat. Nos. 4,286,957 or 4,880,667.

These compounds may be used with other photochromic compounds which are known in the state of the art, such as photochromic compounds giving rise to various colorations such as blue and green. It is thus possible to use spiro(indoline-oxazine)s which are well known in the state of the art.

Once applied to ophthalmic materials or introduced into such materials, the appearance of a coloration is observed after exposure to UV irradiation and the return to the original colour or to the original transparency is observed when the exposure tour radiation is interrupted.

The compounds in accordance with the invention have the advantage of allowing this change in colour to take place a large number of times and at very variable temperatures, of between 0° and 40° C.

The examples which follow are intended to illustrate the invention, but are not limiting in nature.

EXAMPLE 1

Synthesis of 8-ethoxy-2-methylspiro[syn-5,6-benzo-2-azabicyclo-(2,2,2)octane-3,3'-[3H]naphth-[2,1,b][1,4]oxazine]

1st Step

Synthesis of 2,3-dimethyl-8-ethoxy(syn-5,6-benzo-2-azabicyclo-(2,2,2)octane) iodide (1) obtained according to the method of Bradscher (Bradscher C. K.; F. Day; Heterocycl. Chem., 11.23 (1974):

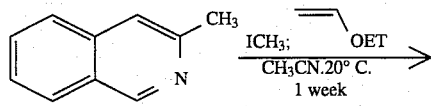

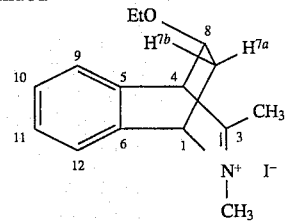

To a solution of 3-methylisoquinoline (0.7 g; 4.9 mmol) in 35 ml of acetonitrile are added 0.5 ml of methyl iodide (7.3 mmol), 2.3 ml of ethyl vinyl ether (24 mmol) and 35 mg of 4-methoxy phenol (0.28 mmol).

The reaction mixture is left stirring for 7 days at room temperature and the desired product is then obtained by precipitation (addition of ethyl ether).

2nd Step

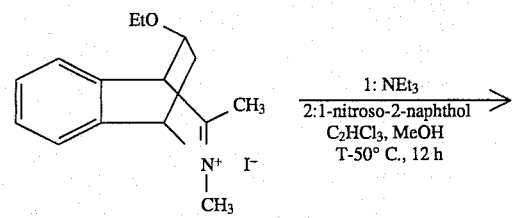

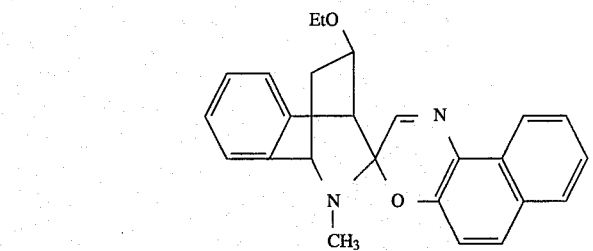

2,3-Dimethyl-8-ethoxy(syn-5,6-benzo-2-azabicyclo-(2,2,2-octane) iodide (0.1 g; 0.28 mmol) is dissolved in 10 ml of trichloroethylene.

One equivalent of triethylamine (0.028 g; 0.28 mmol) is then added, followed by a few drops of methanol (about 1 ml) in order to homogenize the solution.

A solution of 1-nitroso-2-naphthol(0.048 g; 0.28 mmol) in 5 ml of trichloroethylene is added dropwise over 20 minutes at a temperature of 50° C. The reaction mixture is left for 12 hours at 50° C. under a nitrogen atmosphere.

Evaporation of the solvent gives an oil, which is chromatographed by flash chromatography on silica gel, using hexane (95)/ethyl acetate(5) as eluent mixture.

Recrystallization from methanol (T<50° C.) makes it possible to obtain the expected spironaphthoxazine, and to isolate one of the diastereoisomers:

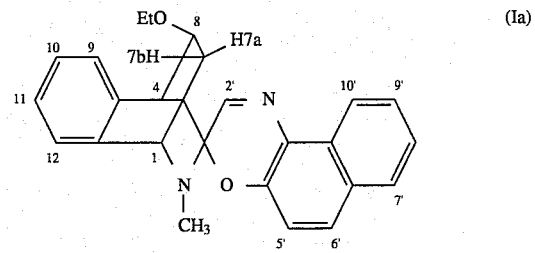

(Ia)

M.p.=137°–8° C.

EXAMPLE 2

Synthesis of 8-ethoxy-2-methyl-9-nitrospiro[syn-5,6-benzo-2-azabicyclo-(2,2,2)octane-3,3'-[3H]naphth-[2,1,b]-[1,4]oxazine]

1st Step

Synthesis of 2,3-dimethyl-8-ethoxy-9-nitro(syn- 5,6-benzo-2-azabicyclo-(2,2,2)octane) iodide (4):

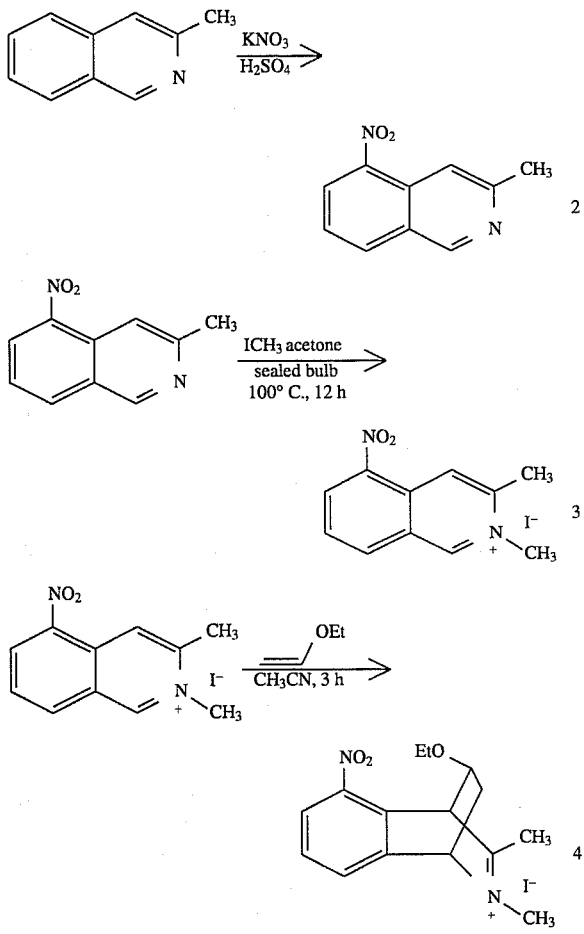

To a solution of 3-methylisoquinoline (0.72 g; 5 mmol) dissolved in 4 ml of sulphuric acid, placed in an ice bath, is added dropwise a solution of potassium nitrate (0.5 g; 5.4 mmol) dissolved in 3 ml of sulphuric acid, while ensuring that the temperature of the reaction medium does not exceed 4° C.

This is then poured into a solution composed of 40 ml of water and 40 g of crushed ice, then neutralized with aqueous ammonia, filtered and recrystallized in ethanol: 3-methyl-5-nitroisoquinoline 2 is obtained.

Quaternization of the nitrogen is carried out in a sealed bulb: to 0.73 g (3.9 mmol) of 3-methyl-5-nitroisoquinoline in 10 ml of acetone are added 1.65 g (11.6 mmol) of methyl iodide.

The mixture is left overnight at 100° C. and, after filtration, 2,3-dimethyl-5-nitroisoquinolinium iodide 3 is recovered.

2,3-Dimethyl-5-nitroisoquinolinium iodide (0.5 g; 1.5 mmol) is dissolved in 10 ml of acetonitrile; 0.546 g (7.6 mmol) of ethyl vinyl ether and 20 mg of 4-methoxyphenol (0.16 mmol) are then added.

The reaction mixture is left for 3 hours at room temperature and the azabicyclic iodide 4 is then collected by precipitation in ethyl ether and filtration.

2nd Step 2,3-Dimethyl-8-ethoxy-9-nitro(syn-5,6-benzo-2-azobicyclo( 2,2,2)octane) iodide (4) (0.1 g; 0.26mmol) is dissolved in 10 ml of trichloroethylene. One equivalent of triethylamine (0.026 g; 0.26 mmol) is then added, followed by a few drops of methanol (about 1 ml) in order to homogenize the solution.

A solution of 1-nitroso-2-naphthol (0.045 g; 0.26 mmol) in 10 ml of trichloroethylene is added dropwise over 20 minutes at a temperature of 50° C. The reaction mixture is left for 12 hours at 50° C. under a nitrogen atmosphere.

Evaporation of the solvent gives an oil, which is chromatographed by flash chromatography on silica gel, using hexane (90)/ethyl acetate(10) as eluent mixture.

Recrystallization from methanol (T<50° C.) makes it possible to obtain the expected spironaphthoxazine (Ib).

8-ethoxy-2-methyl-9-nitrospiro{syn-5,6-benzo-2-azabicyclo-( 2,2,2)octane-3,3'-[3H]naphth-[2,1,b][1,4]oxazine}:

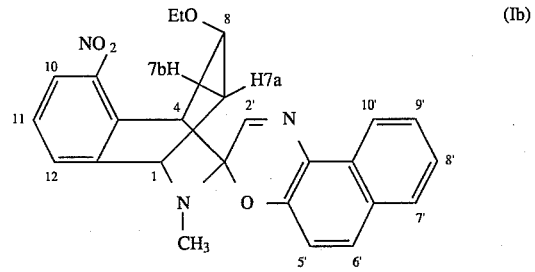

M.p.=139°–143° C.

EXAMPLE 3

Synthesis of 8-methyl-15-nitrospiro [syn-10,11-benzo-8-azatricyclo-( $5,2,2,0^{2,6}$)undec-3-ene-9,3'-[3H]naphth-[2,1,b][1,4]oxazine]

1st Step

Synthesis of 8,9-dimethyl-15-nitro [syn-10,11-benzo-8-azatricyclo-(5,2,2,0$^{2,6}$)undec-3-ene] iodide (5):

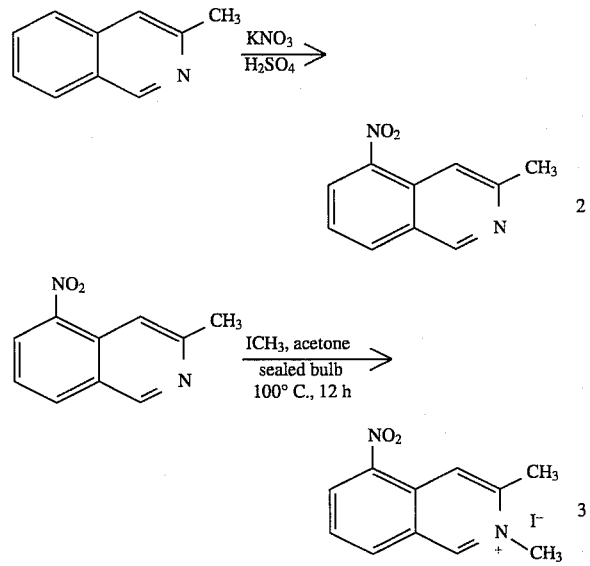

-continued

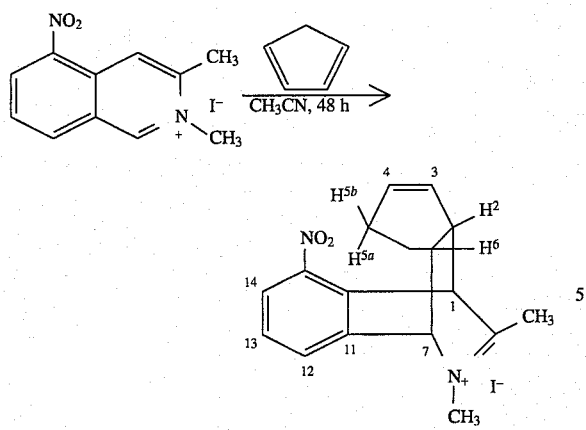

2,3-Dimethyl-5-nitroisoquinolinium iodide 3 (504 mg; 1.53 mmol), the synthesis of which has been described in Example 2, is dissolved in 20 ml of acetonitrile; 403 mg (6.1 mmol) of freshly distilled cyclopentadiene and 5 mg of hydroquinone are then added.

The reaction mixture is left for 2 days at room temperature and the azatricyclic iodide 5 is then collected by precipitation in ether to obtain pure 5.

2nd Step

The condensation reaction is carried out under identical conditions to those of the first two examples; the spirooxazine of formula (Ic) is then obtained:

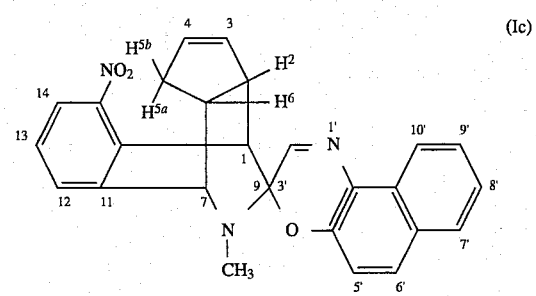

M.p.=175°–178° C.

EXAMPLE 4

The corresponding spiro(azobicyclo-oxazine) was prepared according to a similar procedure to that of Example 1.

8-Ethoxy-9'-methoxy-2-methylspiro{syn-5,6-benzo-2-azabicyclo-(2,2,2) octane-3,3'-[3H]naphth-[2,1,b][1,4]oxazine}:

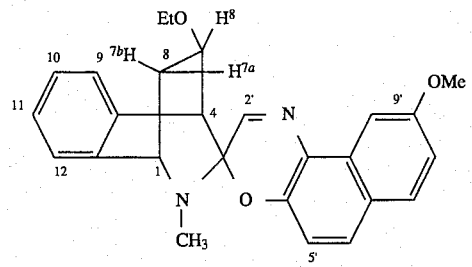

Obtained from the condensation reaction of 3 with 7-methoxy-1-nitroso-2-naphthol.
M.p.=152° C.

EXAMPLE 5

The corresponding spiro(azabicyclo-oxazine) was synthesized according to an experimental procedure identical to that of Example 1, the 1-nitroso-2-naphthol being replaced with 5-nitroso-4-hydroxybenzofuran during the second step. The colour of the photomerocyanin results from a very broad absorption band in the visible region, giving rise to a tint which approaches neutrality.

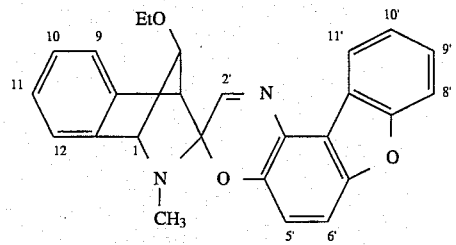

Physical characteristics: M.p.=169° C. $^1$H NMR, 250 MHz, δ(ppm) (CDCl$_3$, T.M.S.): 1.04 (t, 3H, OCH$_2$CH$_3$); 1.46 (bd, 1H, 7a-H); 2.36 (s, 3H, NMe); 2.91 (ddd, 1H, 7b-H); 3.32–3.57 (m, 2H, OCH$_2$); 3.81 (dd, 1H, 1-H); 3.89 (d, 1H, 4-H); 4.58 (ddd, 1H, 8-H); 6.98 (s, 1H, 2'-H); 7.08 (d, 1H, 5'-H); 7.24–7.34 (m, 5H); 7.39 (d, 1H, 6'-H); 7.46 (dd, 1H); 8.28 (d, 1H).

EXAMPLES 6 AND 7

The procedure, from the synthetic viewpoint, is different. Here, the dienophile is introduced onto the isoquinoline moiety (first step). After intramolecular cyclization (second step), the cycloadduct obtained (3 and 4) can then be condensed with 1-nitroso-2-naphthol in order to obtain the corresponding spiro[azapolycyclanenaphthoxazines] (6 and 7).

1st Step

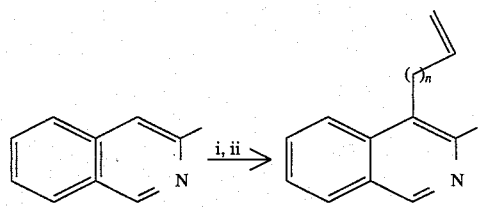

1: n = 3
2: n = 4

(i) Lithium cyclohexylisopropylamide, –73° C.

(ii) n-Bromoalkene, THF, –73° C.→20° C.

This reaction route made it possible to synthesize 3-methyl-4-pent-4-enylisoquinoline 1 and was applied to 3-methyl-4-hex-4-enylisoquinoline 2 with a view to enhancing the steric hindrance.

2nd Step

This consists of a thermolysis of the 4-enylisoquinolines 1 and 2:

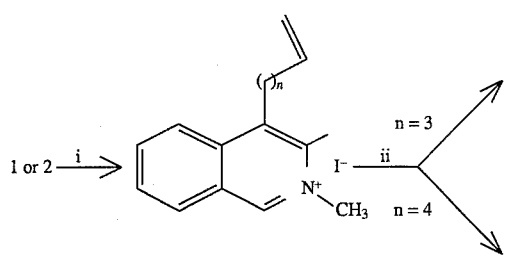
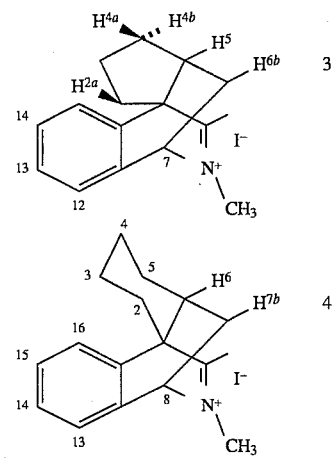

i: CH₃I, acetone, sealed bulb, 100° C.
ii: Acetonitrile, 150° C., 3h.
3rd Step
Synthesis of the spiro[azapolyclane-oxazines]:

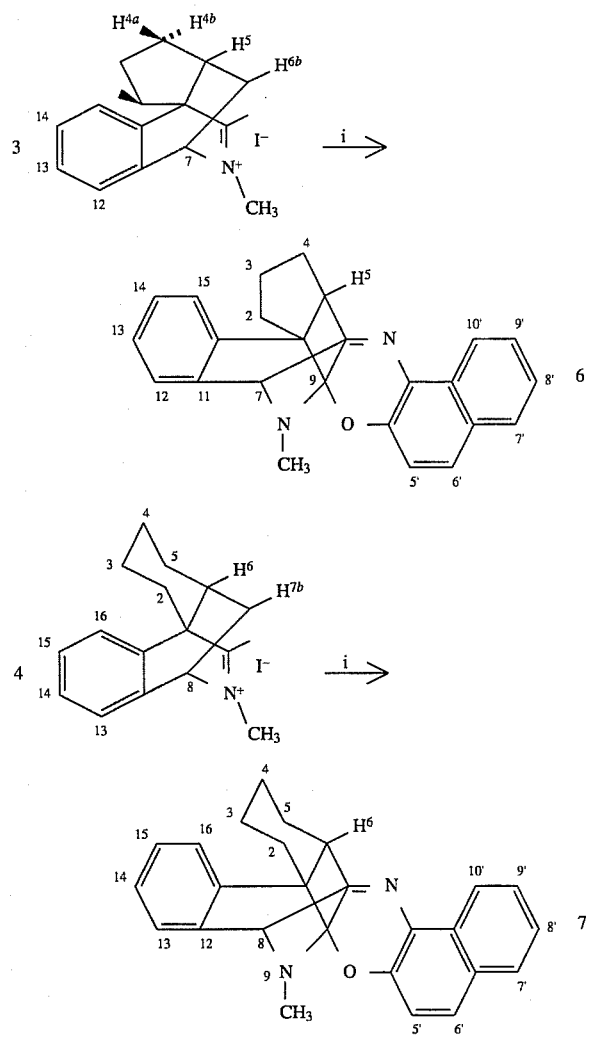

i: Et₃N, 1-nitroso-2-naphthol, trichloroethylene.

| | SPECTROKINETIC PARAMETERS (measured in toluene at 25° C.) | | | |
|---|---|---|---|---|
| | Colour of the photo-merocyanin | $\lambda_{max}$ (nm) and $\lambda_e$ (nm) | Thermal decoloration kinetic constant K in s⁻¹ | $A_o$ (colorability at 2.5 × 10⁻⁵M) |
| Examples | | | | |
| 1 | Pinkish | (535) 563 | 0.36 | 1.3 |
| 2 | Pinkish | (534 (561) | 2.70 | 0.66 |
| 3 | Pinkish | 530–560 | 1.50 | 0.8 |
| 4 | Pinkish | 531–558 | 0.37 | 0.9 |
| 5 | Bluish Gray | (564)–598 (642) | — | — |
| 6 | Pinkish | 552–583 | 4.04 | 1.15 |
| 7 | Pinkish | 561–590 | 13.08 | 0.89 |

The visible-range absorption spectrum of the open form of the spirooxazine is characterized by:

$\lambda_{max}$ (nm): that is to say the wavelength of the absorption maximum.

$\lambda_e$ (nm) indicated in brackets; this is the wavelength corresponding to a shoulder of the spectrum.

We claim:

1. Photochromic compound, characterized in that it corresponds to the general formula:

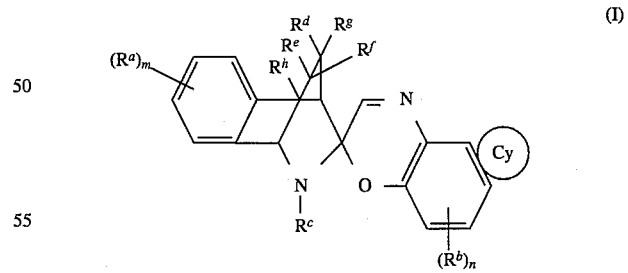

(I)

in which:

$R^a$ and $R^b$ denote, independently of each other, a hydrogen atom; an alkyl group; a group OR, SR, COR or COOR in which R denotes a hydrogen atom, an alkyl or an aryl group; an amino group $NR_1R_2$ in which $R_1$ and $R_2$ denote, independently of each other, a hydrogen atom, an alkyl group, a cycloalkyl group or an aryl group, $R_1$ and $R_2$ optionally forming, with the nitrogen atom, a 4- to 7-membered heterocycle and also optionally containing one or more hetero atoms chosen from sulphur, oxygen and nitrogen; a halogen atom, a $C_1$–$C_4$ polyhaloalkyl group; a group $NO_2$, CN or SCN; $SO_3R'$ where R' denotes hydrogen or an alkali metal;

m denotes an integer from 1 to 4 and n is equal to 1 or 2;

Cy denotes an aromatic ring, preferably a 5- or 6-membered aromatic ring, optionally substituted with one or more groups $R^a$, defined above, or an aromatic or non-aromatic 4- to 7-membered heterocycle containing one or more hetero atoms chosen from nitrogen, oxygen and sulphur, or a benzofuran group;

$R^c$ denotes an alkyl group; an allyl, phenyl or arylalkyl group which is mono- or disubstituted with alkyl, alkoxy or $NO_2$ substituents; an optionally substituted alicyclic group; an aliphatic hydrocarbon group containing one or more hetero atoms such as oxygen, sulphur or nitrogen in its chain;

$R^d$, $R^e$, $R^f$ and $R^g$ denote, independently of each other, a hydrogen atom, an alkyl group, an alkoxy group or a thioalkyl group; two of these radicals optionally forming a 4- to 7-membered cycloalkyl or cycloalkenyl which optionally contains one or more hetero atoms chosen from nitrogen, sulphur and oxygen and which is optionally condensed with a 5- or 6-membered aromatic ring which is optionally substituted with one or more radical $R^a$ and $R^b$, as defined above; and $R^h$ denotes hydrogen or forms with $R^d$ a 5- or 6-membered cycloalkyl.

2. Compound according to claim 1, characterized in that in the formula (I), the alkoxy and alkyl groups contain 1 to 6 carbon atoms; the cycloalkyl groups are cyclohexyl or cyclopentyl; the aryl group is phenyl; the arylalkyl group is benzyl; the polyhaloalkyl group is $CF_3$; the halogen is fluorine, bromine or chlorine;

the aromatic rings are phenyl or naphthyl; the 4- to 7-membered heterocyclic rings are pyridine, pyrimidine, indoline, thiazoline and imidazoline rings which are optionally substituted with an alkyl group, a phenyl or amino group, a carbonyl group or a halogen; the aliphatic hydrocarbon group is substituted with an acid, ester or alcohol function.

3. Compound according to claim 1, characterized in that in the formula (I), the radicals $R^a$ and $R^b$ are chosen from hydrogen or $NO_2$; Cy is a 6-membered aromatic ring which is optionally substituted with an alkoxy group; $R^c$ is an alkyl group; $R^d$, $R^e$, $R^f$ and $R^g$ denote an alkoxy group or two of these radicals form a cycloalkenyl.

4. Compound according to claim 1, characterized in that said compound is of one of the general formulae:

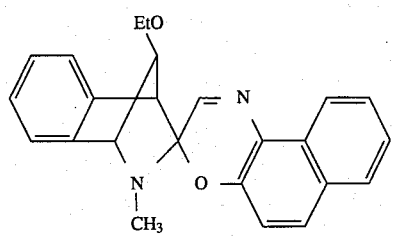
(Ia)

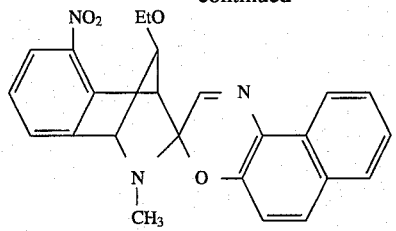
(Ib)

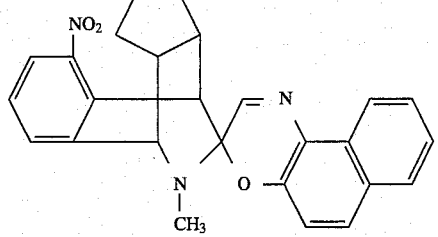
(Ic)

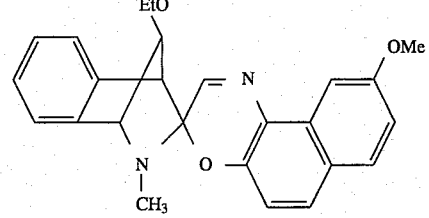
(Id)

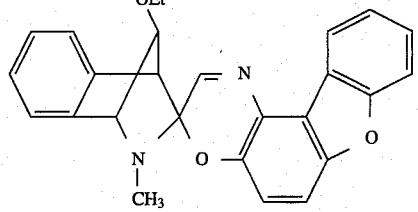
(Ie)

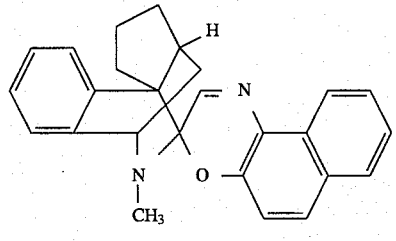
(If)

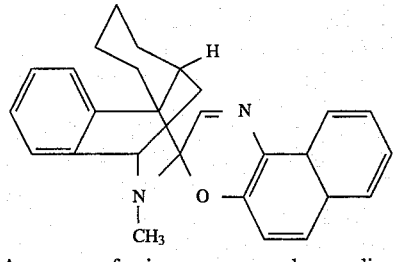
(Ig)

5. A process of using a compound according to any one of claims 1 to 4, as a photochromic compound in ophthalmic optics.

6. Composition for applying to or introducing into a transparent organic polymer material, characterized in that said composition contains at least one photochromic compound as defined in any one of claims 1 to 4, in amounts which are sufficient to enable the material to change colour when exposed to ultraviolet radiation.

7. Composition according to claim 6, characterized in that the composition is in the form of a liquid containing the at least one photochromic compound in dissolved or dispersed form in a solvent-based medium, said compounds being suitable for application to or introduction into a transparent polymer material.

8. Composition for applying to or introducing into a transparent organic polymer material, characterized in that said composition consists of a colourless or transparent solution based on transparent polymers, transparent copolymers or a mixture of transparent polymers in a suitable organic solvent, containing at least one photochromic compound as defined in any one of claims 1 to 4, in amounts which are sufficient to enable the material to change colour when exposed to ultraviolet radiation.

9. Solid transparent material for producing ophthalmic lenses, characterized in that the solid transparent material comprises at least one photochromic compound as defined in any one of claims 1 to 4, in amounts which are sufficient to enable the material to change colour when exposed to ultraviolet radiation.

10. Solid transparent material according to claim 9, wherein said material comprises 0.07 to 20% by weight of photochromic compounds.

11. Solid transparent material comprising a photochromic compound as defined in any one of claims 1 to 4, used in conjunction with other photochromic compounds giving rise to various colorations.

12. Transfer varnish, comprising at least one compound as defined in any one of claims 1 to 4.

* * * * *

UNITED STATES PATENT AND TRADEMARK OFFICE
CERTIFICATE OF CORRECTION

PATENT NO. :   5,529,725
DATED      :   June 25, 1996
INVENTOR(S):   R. GUGLIELMETTI et al.

It is certified that error appears in the above-identified patent and that said Letters Patent is hereby corrected as shown below:

In the Abstract; in column 3, lines 1-13; and in column 14, lines 14-57, formula I is:

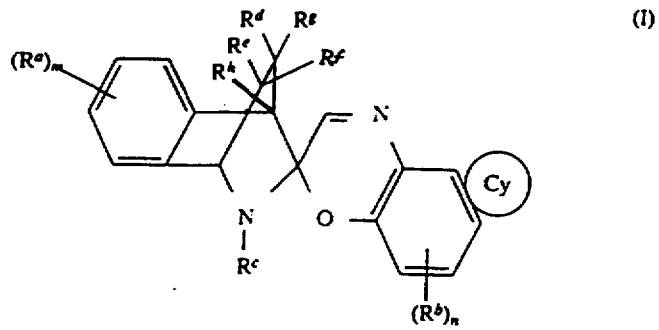

(I)

Signed and Sealed this

Eleventh Day of March, 1997

Attest:

BRUCE LEHMAN

Attesting Officer    Commissioner of Patents and Trademarks